United States Patent
Lewis et al.

(10) Patent No.: US 6,352,535 B1
(45) Date of Patent: *Mar. 5, 2002

(54) METHOD AND A DEVICE FOR ELECTRO MICROSURGERY IN A PHYSIOLOGICAL LIQUID ENVIRONMENT

(75) Inventors: Aaron Lewis; Daniel Palanker; Igor Turovets, all of Jerusalem (IL)

(73) Assignee: Nanoptics, Inc., Jerusalem (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/269,408

(22) PCT Filed: Sep. 25, 1997

(86) PCT No.: PCT/US97/16927

§ 371 Date: Apr. 8, 1999

§ 102(e) Date: Apr. 8, 1999

(87) PCT Pub. No.: WO98/12974

PCT Pub. Date: Apr. 2, 1998

(51) Int. Cl.$^7$ ................................................. A61B 18/18
(52) U.S. Cl. ............................ 606/45; 606/48; 607/104
(58) Field of Search ........................ 606/41, 42, 45–50, 606/169, 2.5; 601/3, 4; 607/100–105; 604/114

(56) References Cited

U.S. PATENT DOCUMENTS

| | | | | |
|---|---|---|---|---|
| 4,301,802 A | * | 11/1981 | Poler | 606/48 |
| 4,476,862 A | * | 10/1984 | Pao | 606/50 |
| 4,597,388 A | * | 7/1986 | Koziol et al. | |
| 4,674,499 A | * | 6/1987 | Pao | 606/50 |
| 4,805,616 A | * | 2/1989 | Pao | 606/50 |
| 5,009,656 A | * | 4/1991 | Reimels | 606/48 |
| 5,089,002 A | * | 2/1992 | Kirwan, Jr. | 606/50 |
| 5,254,121 A | * | 10/1993 | Manevitz et al. | 606/128 |
| 5,318,563 A | * | 6/1994 | Malis et al. | 606/38 |
| 5,697,882 A | * | 12/1997 | Eggers et al. | 604/114 |
| 5,749,871 A | * | 5/1998 | Hood et al. | 606/50 |
| 5,766,153 A | * | 6/1998 | Eggers et al. | 604/114 |

* cited by examiner

Primary Examiner—Michael Peffley
(74) Attorney, Agent, or Firm—Jones, Tullar & Cooper, PC

(57) ABSTRACT

A method and device for electrical emulation of pulsed laser is disclosed. The device utilizes high voltage electrical discharges of sub-microsecond duration in a liquid medium to produce cavitation bubbles of sub-millimeter size for use in high speed precision cutting. Such bubbles are produced by a micro-electrode (1.6) having a central wire having a diameter of 1 microns to 100 microns embedded in an insulator. A coaxial electrode (1.9) surrounds the insulator, and may be spaced from the outer surface of the insulator to provide a path for removing tissue.

25 Claims, 5 Drawing Sheets

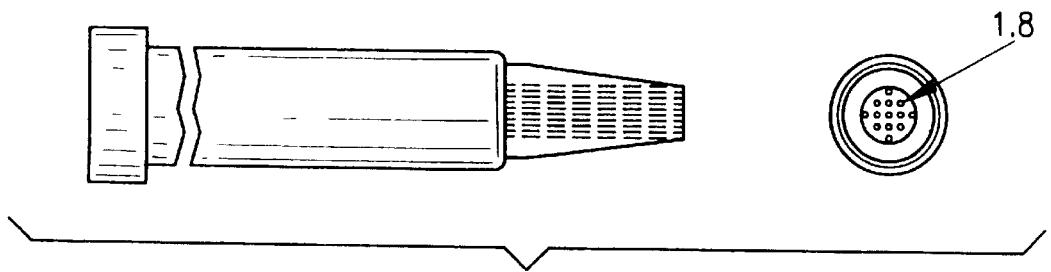
FIG. 3A
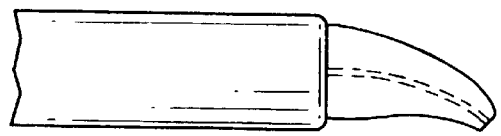
FIG. 3B
FIG. 3C
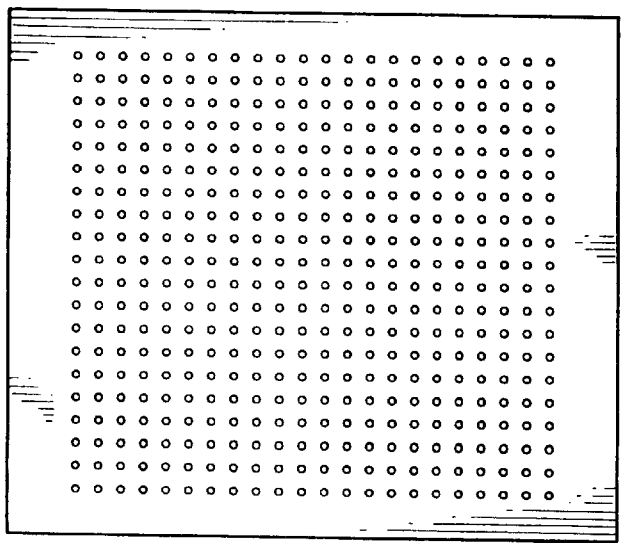 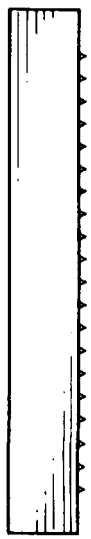
FIG. 4A  FIG. 4B

- 1 Umax=0.3 kV
- 2 Umax=0.5 kV
- 3 Umax=0.7 kV

- 4 Umax=0.9 kV
- 5 Umax=1.1 kV
- 6 Umax=1.4 kV
- 7 Umax=2.7 kV

METHOD AND A DEVICE FOR ELECTRO MICROSURGERY IN A PHYSIOLOGICAL LIQUID ENVIRONMENT

FIELD OF THE INVENTION

The invention is a method and a device that allows for the electrical emulation of the microsurgical abilities of pulsed lasers. These lasers are the basis for new laser procedures that are responsible for high speed and high precision cutting action in biological liquid environments with minimal damage to the surrounding mechanism. They work by producing cavitation bubbles. The action of these lasers and laser procedures are simulated in the current invention by using protocols that are a part of this invention. These protocols regulate the electrical current injected into the specialized device that has been devised. As a result it is possible to emulate the cavitation bubble formation cutting that has become a hallmark of various pulsed laser procedures. The invention allows the same device to be used for such an emulation of these cavitation bubbles while also allowing for heat induced coagulation and poration of biological materials.

BACKGROUND OF THE INVENTION

Various pulsed lasers have been applied to soft tissue cutting and removal in a liquid environment. Three basically different mechanisms of light absorption have been involved in laser surgery: (1) linear absorption of light by tissue (I. Turovets, D. Palanker, Y. Kokotov, I. Hemo, A. Lewis, *J. Appl. Phys.* 79(5): 2689–2693 (1996); D. Palanker, I. Turovets, A. Lewis, *Laser-Tissue Interaction VII, Proc. SPIE* 2681 (1996)); (2) linear absorption of light by the medium (P. D. Brazitikos, D. J. D'Amico, M. T. Bernal, A. W. Walsh, *Ophthalmology* 102 (2): 278–290 (1994); C. P. Lin, D. Stern, C. A. Puliafito, *Invest. Ophthalmol. Vis. Sci* 31(12): 2546–2550 (1990)); or (3) non-linear absorption by tissue or medium associated with dielectric breakdown of the material (A. Vogel, S. Busch, K. Jungnickel, R. Birngruber, *Lasers Surg. Med.* 15: 32–43 (1994)). In spite of differences in the mechanisms of laser radiation absorption in tissue, the mechanism of tissue disruption with pulsed lasers has been generally associated with an explosive expansion of overheated liquid and subsequent cavitation bubble formation. As a result, material disruption occurs in the light absorption zone and in a zone of fast expansion and collapse of cavitation bubbles (I. Turovets, D. Palanker, Y. Kokotov, I. Hemo, A. Lewis, *J. Appln. Phys.* 79(5): 2689–2693 (1996); P. D. Brazitijos, D. J. D'Amico, M. T. Bernal, A. W. Walsh, *Ophthalmology* 102(2): 278–290 (1994); and A. Vogel, S. Busch, K. Jungnickel, R. Birngruber, *Lasers Surg. Med.* 15: 32–43 (1994)).

In view of the general complicated nature of laser-based devices a search was made for ways to emulate with non-laser methodologies the mechanisms that are known to occur with available lasers. In the case of cavitation bubble generation it is known, as described above, that these bubbles result from local and fast heat energy deposition. Thus, it is logical to consider an overheating of a conductive medium with a short pulse of electric current in order to generate an action which is similar to such pulsed laser. The invention described herein realizes such electro microsurgery in a physiological medium with a specific potential for applications in ophthalmology. Previous investigators who have considered pulsed electrical techniques and have seen cavitation bubble formation (R. Vorreuther, R. Corleis, T. Klotz, P. Bernards, U. Englemann, *J. Urology* 153: 849–853 (1995); R. Lemery, T. K. Leung, E. Lavallee, A. Girard, M. Talajic, D. Roy, M. Montpetit, *Circulation* 83(1): 279–293 (1991)) considered these bubbles either as an undesired side effect or as a means for shock wave generation for hard tissue destruction. These electrosurgical devices were designed for relatively high energy pulse generation: between 25 mJ and 40 J and with relatively long pulse duration: hundreds of microseconds. Such high energy pulses resulting in a few millimeter-sized cavitation bubbles cannot be applied to microsurgical applications such as those envisioned in delicate organs such as the eye. To accomplish such delicate cavitation bubble based microsurgery, a new electrical system based on an asymmetric microelectrode that enables generation of hundreds of thousands of cavitation bubbles, is described. This can become an alternative to endo-laser equipment in such areas as vitreoretinal surgery.

The concept can also be extended to the electroporation of individual cells and assemblies of cells in which the state of the prior art is a macroscopic device with macroscopic electrodes placed in a large bath with a solution of cells (M. Joersbo and T. Brunstedt, *Physiologia Plantarium* 81: 256–264 (1991)). Instead of this a microelectrode for local electroporation of individual cells is used, or alternatively, an array of microelectrodes could be applied for poration of assemblies of cells.

In addition, by varying the nature of the characteristics of the electrical current the same device can be used for cavitation bubble cutting, electroporation or coagulation.

STATE OF PRIOR ART

Electrosurgical devices are widely used in surgery. The majority of these techniques are based on heating the tissue by an RF current and this local heat deposition causes one of the following processes: coagulation, and/or water evaporation. As a result, the only capability of such devices is to cut soft tissues by heat deposition which causes significant coagulation in the area surrounding the cut tissue. Such devices are totally useless for endolaser applications, for example in the eye. In addition to such RF techniques, DC pulsed electrical methodologies have not achieved a widespread acceptance because the absence of coagulation was considered an undesirable effect. In the past, cavitation bubbles were generated by DC pulsed methodologies. However, these techniques, which were designed for relatively high energy pulse generation (tens of milliJoules) with relatively long pulse durations (hundreds of microseconds), were only used as a means for shock wave generation for hard tissue destruction (R. Vorreuther, R. Corleis, T. Klotz, P. Bernards, U. Engelmann, *J. Urology* 153: 849–853 (1995)). These high energy pulses resulted in cavitation bubbles with dimensions of a few millimeters, and these have no applicability to, for example, eye microsurgery in which considerably smaller bubbles are required. Laser-based techniques indicate that the pulse energies required to produce such bubbles are in the range of a few tens of microJoules and the pulse durations required are generally in a sub-microsecond range (D. Palanker, I. Hemo, I. Turovets, H. Zauberman, A. Lewis, *Invest Ophthal. Vis. Sci.* 35: 3835–3840 (1994); C. P. Lin, Y. K. Weaver, R. Birngruber, J. P. Fujimoto, C. A. Puliafito, *Lasers Surg. Med.* 15: 44–53 (1994)). In addition to these differences in the time/energy characteristics of the available DC pulsed technologies as compared the present invention, it is required that any device for applications such as vitreoretinal surgery should be able to withstand tens of thousands of pulses. The previous high energy devices described above have a lifetime of less than 100 pulses (R. Vorreuther, R. Corleis, T. Klotz, P. Bernards, U. Engleman, *J. Urology* 153: 849–853 (1995) and this is by far not sufficient for the microsurgical applications that are envisioned.

In terms of cell poration, the prior art were again macroscopic devices with macroscopic electrodes placed in a large bath (M. Joersbo and J. Brunstedt, *Physiologia Plantarium* 81: 256–264 (1991)) with a solution of cells.

SUMMARY OF THE INVENTION

The method and device of the present invention are based on producing submicrosecond high voltage discharges in physiological media with special protocols designed for the generation of cavitation bubbles for soft tissue microsurgery in a liquid environment as is possible today with certain pulsed lasers. The device consists of a combination of three elements:

a specific microelectrode structure, specific electrical protocols to develop the required pulse characteristics to emulate pulsed laser microsurgery with cavitation bubble generation in the same device that can produce other electrical protocols for tissue coagulation and electroporation; and the above protocols determine the characteristics of the HV pulse generator that is to be used.

DESCRIPTION OF THE INVENTION

The foregoing features of the invention are illustrated in the accompanying drawings, in which:

FIG. 3A is a schematic illustration of a microelectrode in accordance with the invention, having multiple wires;

FIG. 3B is a schematic illustration of a partially bent, single-wire microelectrode in accordance with the invention, having a flat tip;

FIG. 3C is a schematic illustration of a single-wire side-firing microelectrode in accordance with the invention, having a flat tip;

FIG. 4A and 4B are schematic top and side views, respectively, of a microelectrode array;

Figure 1A:
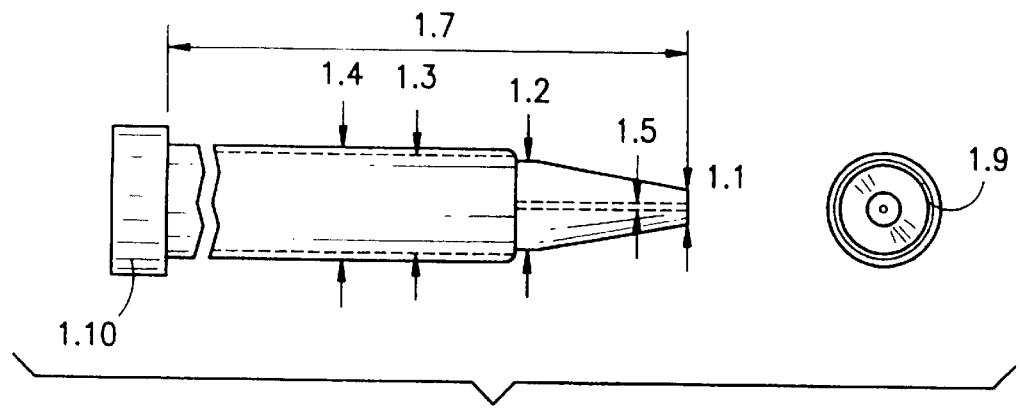
FIG. 1A is a schematic illustration of a microelectrode in accordance with the invention, utilizing a single wire and having a tapered insulator with a flat tip.
Figure 1B:
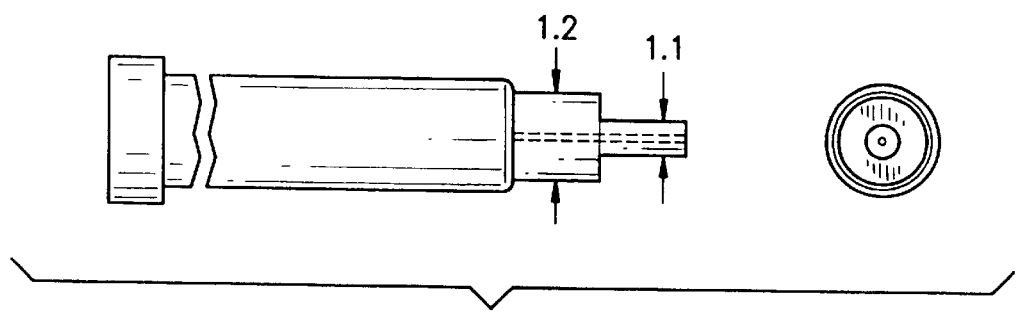
FIG. 1B is a schematic illustration of a microelectrode in accordance with the invention, utilizing a single wire and having a nontapered insulator with a flat tip.
Figure 1C:
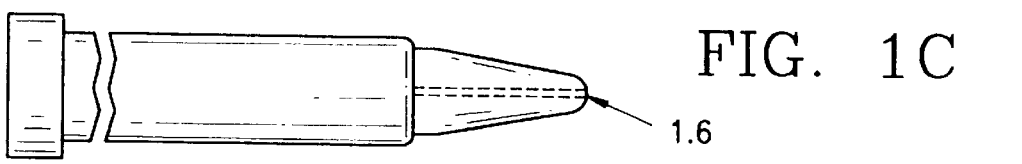
FIG. 1C is a modification of the device of FIG. 1A, wherein the insulator has a rounded tip.
Figure 1D:
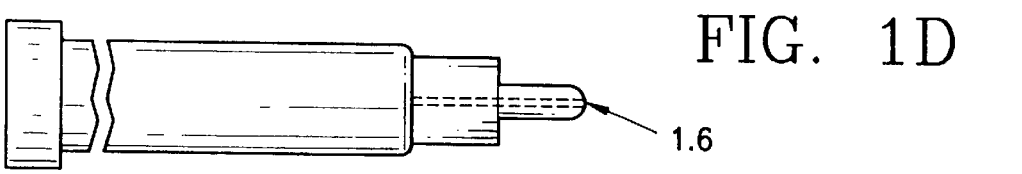
FIG. 1D is a modification of the device of FIG. 1B, wherein the insulator has a rounded tip.
Figure 6:
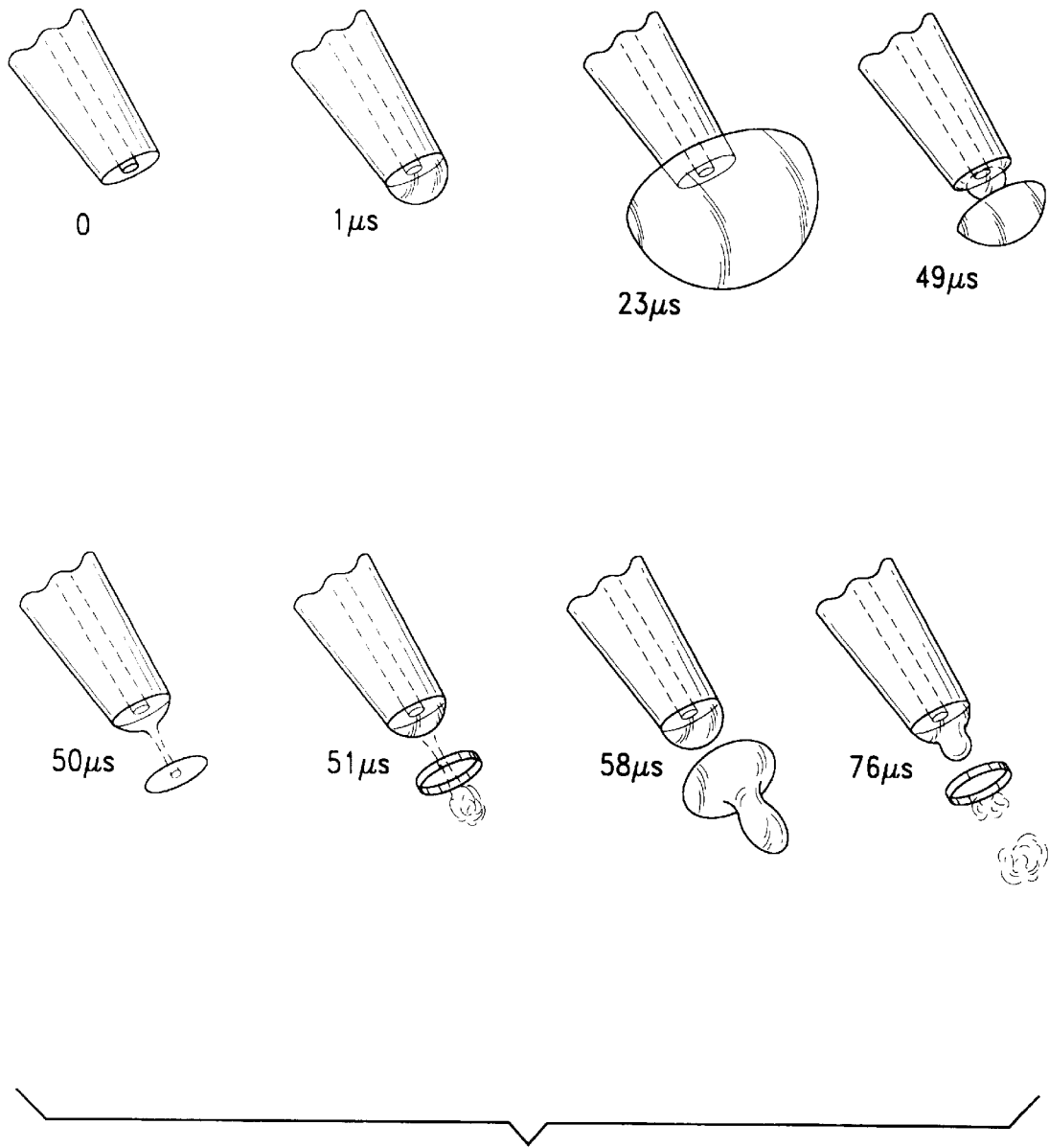

FIG. 6 is a sequence of micrographs illustrating the dynamics of cavitation bubbles generated at a potential ($U_{max}$) of 2.7 kV, utilizing an electrode having a wire diameter of 20 $\mu$m and a tip diameter of 200 $\mu$m, at a magnification of 100×, the delay between the electric pulse and the flash pulse being shown in $\mu$s in each frame The Microelectrodes One way to form the microelectrodes, or needles, of the present invention is to seal a thin metal wire (1.5) into an insulator (1.2) with a variety of structures that can be tapered (FIGS. 1A & 1C) or have other geometries (FIGS. 1B & 1D). The wire (1.5) has a diameter at its exit from insulator (1.2) in the range of 1–100 microns. This insulator (1.2) and wire (1.5) creates an internal (main) electrode (1.1). A second electrode (1.3) is provided to mechanically protect the main electrode. This may be formed by coating the surrounding insulator (1.2) with a metallic coating (1.3) (see FIG. 1A). The resulting external electrode can play the role of a protective metal cover for the main inner electrode (1.1). The geometry of this microelectrode and its connection to the output terminals (2.1) and (2.2) of the HV pulse generator (2.3) are schematically shown in FIG. 2.

Figure 2:
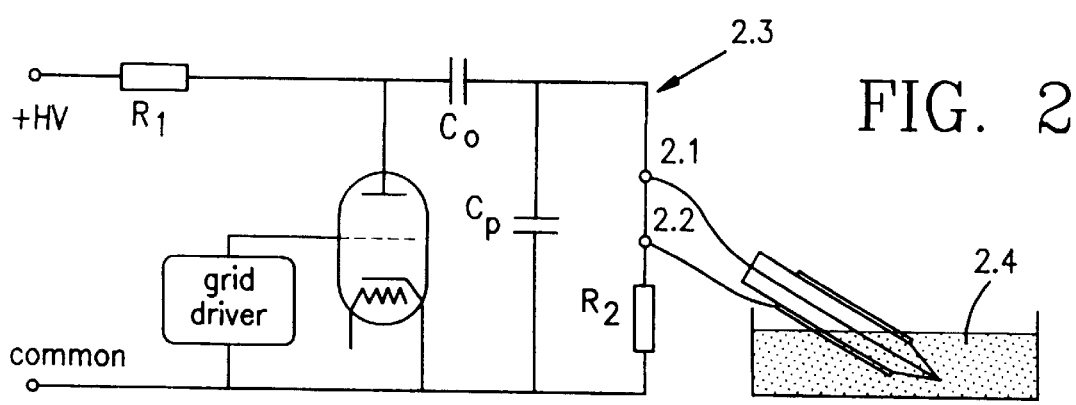
FIG. 2 is a schematic diagram of a high voltage generator connected to the microelectrode of FIGS. 1A–1D.

As shown in FIG. 2, the main electrode is placed in a conducting medium (2.4). The high voltage (HV) generator (2.3) produces electrical submicrosecond duration discharges through a gas layer in the conducting liquid-containing environment which produces cavitation bubbles with characteristics which emulate the action of pulsed lasers in a liquid medium. The bubbles are of sub-millimeter sizes. Such cavitation bubbles provide a mechanism for soft tissue microsurgery in a physiological medium, such as in the eye.

The microelectrode may be fabricated by pulling a glass microcapillary tube having a metal wire inside the tube. The tube is heated and pulled to produce the tapered shape of FIG. 1A, with the glass forming the insulator (1.2). Alternatively, the microelectrode can be fabricated using microlithography. The device may be used as a single device or multiple microelectrodes may be mounted in an array, as illustrated in FIGS. 4A and 4B, for use in microcutting or microperforation of materials, such as aggregates of cells.

The outer dimensions of the microelectrode (1.4) can be chosen according to the requirements of the application. For example, for microsurgical applications they could be similar to that of laser tips applied in endolaser microsurgery.

The diameter of the insulator around the exit of the main electrode (1.1) should be large enough to have mechanical strength while preventing the puncture of soft tissue. On the other hand, it should be small enough to enable it to reach the tissue to be cut at various angles. These requirements determine the range of the diameter of electrode (1.1) to be: 0.05–0.4 mm. It is useful to have rounded edges of the insulator (FIG. 1C, 1.6) in order to keep the electrode wire (1.5) in close proximity to the treated tissue when the tip is held at different angles relative to the tissue surface. The diameter of insulator (1.2) inside the second electrode (1.3) should be as large as possible to decrease the capacitance of the electrodes in the conductive liquid environment, and could be equal to the inner diameter of the external electrode (1.3). In certain cases (1.2) could be smaller than (1.3) in order to provide a gap (1.9) between electrode 1.3 and insulator (1.2) (FIG. 1A) to allow suction during the treatment. Such suction allows lifting of treated tissues and the evacuation of gas bubbles and tissue debris that results from tissue cutting by the generated bubbles.

The outer diameter of the second (external) electrode (1.4) should be 0.9–1 mm, as this is standard equipment for instruments used in certain microsurgical procedures used in vitreoretinal surgery.

The total length (1.7) of the microelectrode (FIG. 1A) is 38–40 mm to allow for access to all the areas inside the eye ball for such vitreoretinal surgery. Other microsurgical procedures may require other dimensions.

The same structure could be used with, for example, a set of multiple wires as the inner electrode (see FIG. 3A, 1.8) or the tip can be partially bent in order to fire the cavitation bubble at an angle (FIG. 3B) or can have a geometry that can produce a cavitation bubble at right angles to the axis of the electrode (FIG. 3C). All the electrode configurations shown in FIGS. 3A–3C can also have electrode and insulator geometries with the structures that are seen in FIGS. 1A–1D.
Electrical Protocols to Emulate Pulse Laser Induced Cavitation Bubbles To achieve the high cutting efficiency of the pulsed laser treatments that are currently being developed, cavitation bubbles should be created fast enough for generation of high pressures and high boundary velocity and acceleration. These requirements determine the minimal peak power of the pulse. On the other hand, the cutting action should be local enough for prevention of extensive damage in the surroundings of a lesion. This requirement limits the total energy imposed on the bubble formation. Based on the experience of laser-induced cavitation (D. Palanker, I. Hemo, I. Turovets, H. Zauberman, A. Lewis, *Invest Ophthal. Vis. Sci* 35: 3835–3840 (1994); C. P. Lin, Y. K. Weaver, R. Birngruber, J. G. Fujimoto, C. A. Puliafito, *Lasers Surg. Med.* 15: 44–53 (1994)), the diameter of the cavitation bubble required for precise and effective cutting of vitreoretinal tissue should be in a range of 0.4–0.5 mm, that corresponds to the bubble energies in a range of 3 to 6 µJ.
The High Voltage Pulse Generator The foregoing protocols determine the characteristics of the high voltage pulse generator. The electrode diameter 1.5 has to be capable of generating single pulses and pulse trains with a pulse duration varying in a range of 30 ns–3 µs, and the generator must be capable of varying the voltage amplitude in the range of 100 V–10 kV. The peak current during the pulse can reach a few Amperes.

In addition to pulse generation aimed at cavitation bubble generation and tissue cutting, electrical pulses with lower voltage and, possibly, longer pulse duration could be applied with the above electrodes for electroporation of individual cells or for cell layers. Furthermore, the electrical power supply can also be amended so that this invention can also have the added capability of a coagulation.
Extension of the Invention to Parallel Devices Similar electrode geometries and pulse protocols can be envisioned to produce a parallel array of electrodes for the generation of a parallel array of cavitation bubbles and/or heating for producing bioelectromechanical field effects on multiple biological cells at one time (see FIG. 4).
Applications of the Device Numerous applications of the invented device are possible in the field of soft tissue microsurgery based on the cutting action of the generated cavitation bubbles. One of the most promising for the single electrode is vitreoretinal membrane removal, because the accepted mechanical peeling and cutting of such membranes is often associated with retinal damage. Furthermore, the present device can be used in all microsurgical procedures in physiological media (or other conducting liquids), including microsurgery of the internal organs.

In addition, with the modified electrical characteristics the device could also be used for bioelectromechanical effects of individual cells and cell layers, and coagulation of tissue.

Furthermore, the bent, cantilevered tips that produced in this invention can be of considerable value in other areas of science and technology. For example, such cantilevered electrodes can be produced such that the cantilever is very flexible (Force constants of a few N/m) and the tip is very small (0.05 µ). With such an extension of the present methodology, together with the pulsed protocols that have been developed, and that have been described herein, controlled alteration of surfaces can be effected that will allow fine lithographic patterning of such surfaces.
Experiments
Analysis of the Modes of the Electrical Discharge of the Device The pulse protocols that have been invented and are described herein were developed as a result of detailed experimentation that allowed close emulation of the effects of pulsed laser cavitation bubble generation.

Figure 5A:
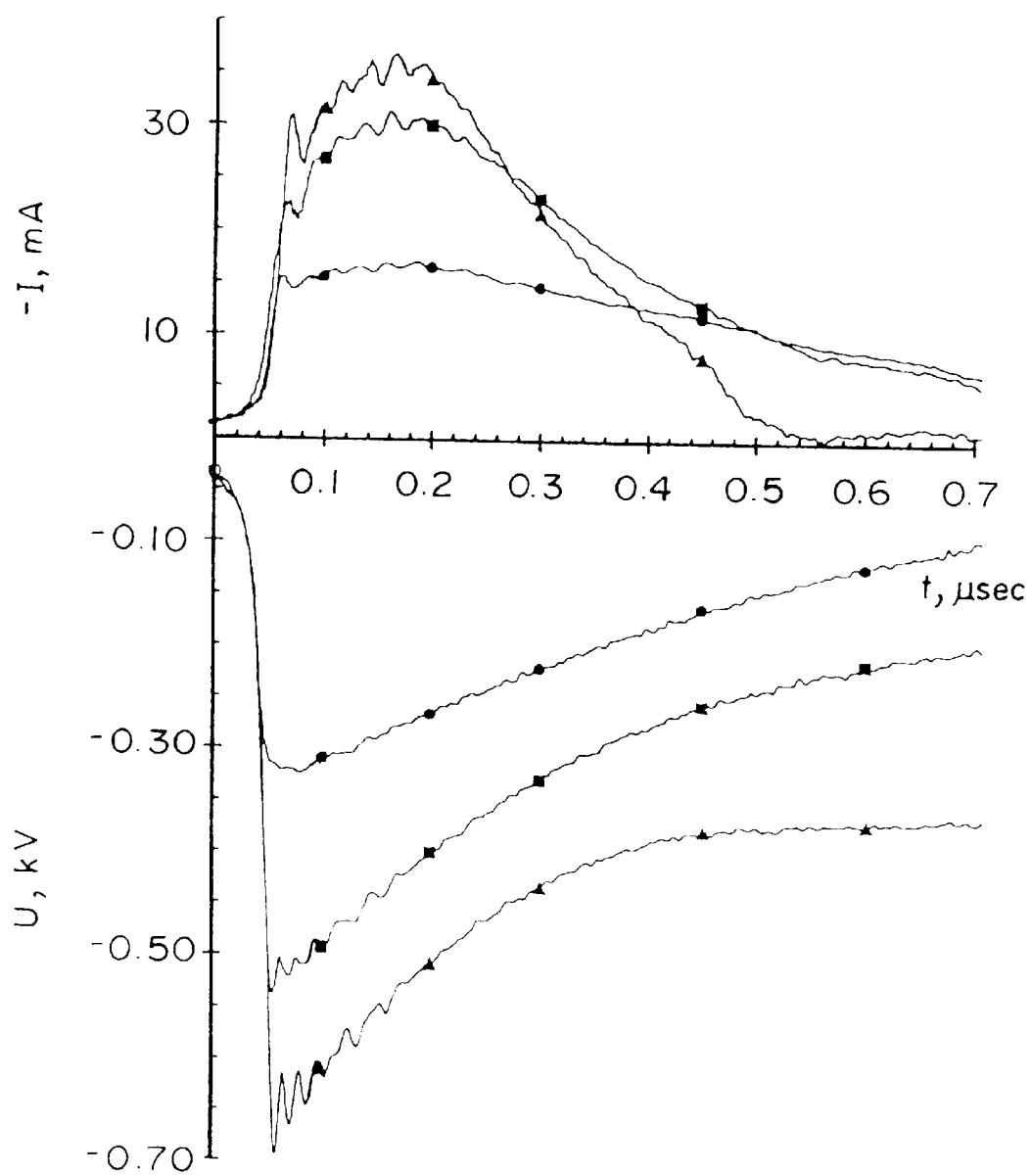
FIG. 5A is a graphical illustration of the time dependence of electrode potential (U) and current passing through the exit surface of an electrode (-I) during a discharge, the electrode having a wire diameter of 25 $\mu$m.
Figure 5B:
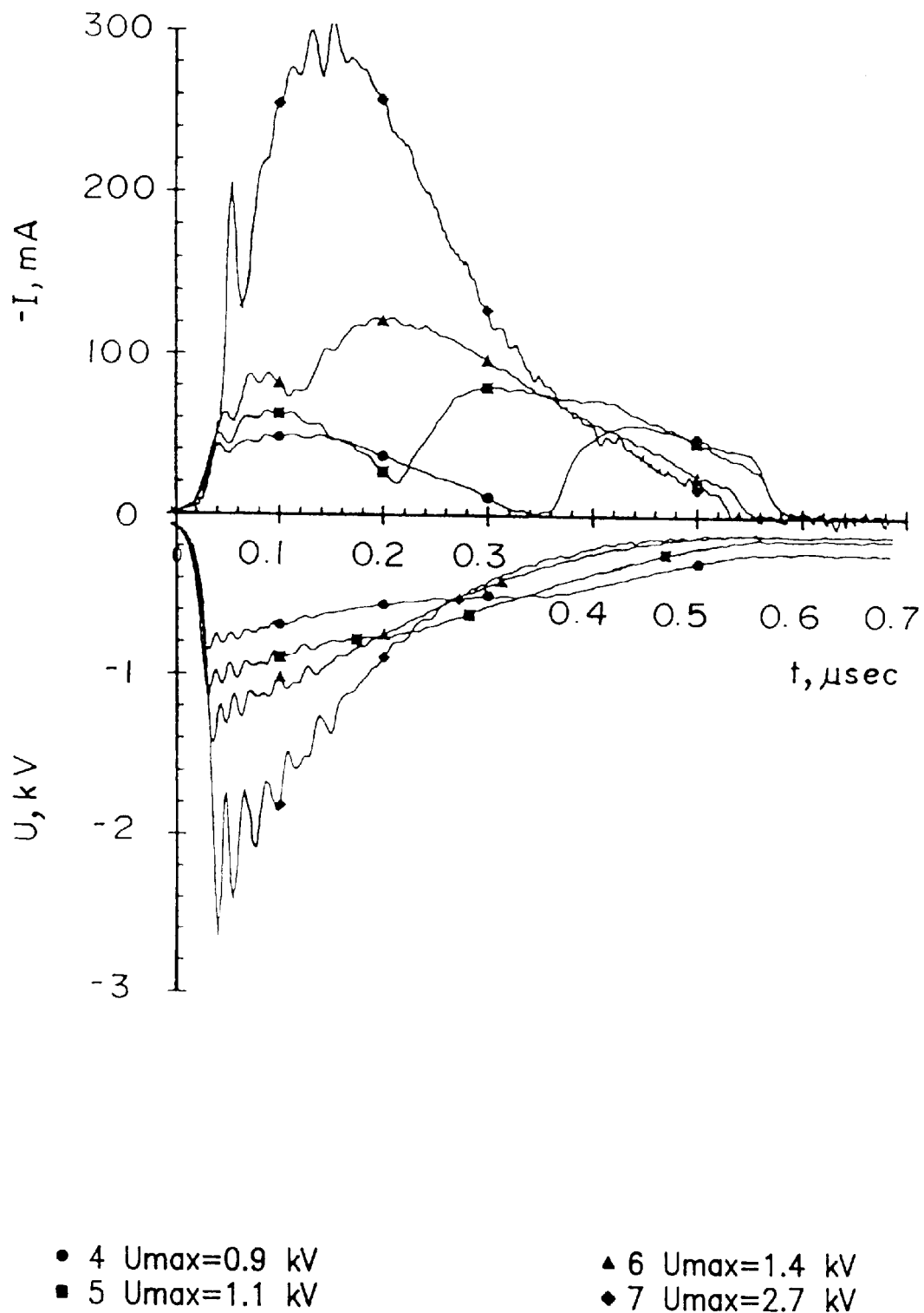
FIG. 5B is a graphical illustration of a second discharge, following that illustrated in FIG. 5A.

Specific examples of these experiments are described in this section. For example, for an electrode with a wire diameter (1.5) of 25 µm the pulse profiles of the electrode potential (U) and the current passing through the exit surface of the electrode (I) are presented in FIG. 5. At $U_{max}$=0.3 kV (FIG. 5A, curves 1) the voltage and current simultaneously decrease with a time constant of about 0.6 µs. As the potential increases, the nature of the discharge changes: The current drops much faster after about 0.2 µs, resulting in slowing down the voltage reduction (FIG. 5A, curves 2). At $U_{max}$=0.7 kV (FIG. 5A, curves 3), the current falls to zero (switched off) when the potential is still at half of the maximum. This switching off of the current results from gas generation on the surface of the electrode that disconnects the liquid from the metal surface.

As the electric field in the gas layer becomes high enough, an electron avalanche is generated in this layer, that then propagates inside the liquid. This results in the second pulse of current generated after the first one (see FIG. 5B), and with increase of the voltage the delay between these two pulses decrease. At $U_{max}$ higher than 1.4 kV (FIG. 5B, curve 6), these two pulses completely overlap and at $U_{max}$ 2.7 kV (FIG. 5B, curve 7), they became indistinguishable. The discharge at the voltage range of 1.4–2.7 kV was accompanied by an emission of reddish light and a sound wave generation. At $U_{max}$=2.6 kV, the dimensions of the lighted spot was about 7 µm. The best emulation of the laser cutting was achieved with a range of high voltage that is 2–2.7 kV.
Cavitation Bubble Dynamics The sequence of micrographs of cavitation generated at the electrode with a 20 µm wire at $U_{max}$=2.7 kV is shown in FIG. 6. The delay time between the electric pulse and the flash of the dye laser is shown (in µs) in the corner of each frame. The spark generated in the vicinity of the electrode is clearly seen as a white spot in front of the wire. The average velocity of the bubble boundary during the first 1 µs of the growth phase (frames 1,2) was about 90 m/s. The primary cavitation bubble grew in about 25 µs (frames 2,3) reaching the maximal diameter of about 0.5 mm. During the collapse, the bubble had a mushroom-like shape (frame 4) that was eventually transformed to a ring and a stem connecting its center with the center of the tip (frame 5). The secondary bubbles were generated from both the ring and the stem (frames 6,7). These bubbles were ejected away from the tip at different velocities (about 5 and 17 m/s, respectively) and then collapsed and disappeared at distances of about 0.25 and 0.65 mm, respectively, at about 76 µs after the pulse (frame 8).

Tissue Cutting

Post-mortem fresh bovine eyes were prepared as an eyecup preparation: the anterior segments of the eyes and vitreous were removed and the eyecup was filled with Hartmann's physiological solution. For measurements of a cutting rate, 4–5 cuts of about 1 cm length were produced at the repetition rate of 30 Hz. Cutting efficiency was determined at the speed of the full depth cutting of retina. Cutting of retina with the rate exceeding 1 mm/s was observed at pulse energies of about 80 µJ/pulse with the electrode wire diameter varying in a range 10–25 µm. The retinal tissue in the immediate vicinity of the ablated region looked normal, and the borders of the lesion were quite sharp and clean.

These experiments are the first step in demonstrating a variety of delicate surgical procedures that will evolve as a result of the application of this new device and method. For example, the microelectrode (1.1) can be connected to a catheter (1.10) or other support mechanism for manipulation. If desired, the gap 1.9 may serve as a conduit for the delivery of drugs to the regions of the tip of the microelectrode. Such delivery can be done simultaneously with the bubble cutting of the tissue.

What is claimed is:

1. A device consisting of:
    a microelectrode formed of a single metal wire inside an insulator, said insulator having a diameter of less than about 1 mm and said wiring having an exit diameter of less than 100 microns;
    a second electrode surrounding said insulator; and
    a high voltage pulse generator capable of producing a voltage in the range of 100 V to 10 kV connected between said wire and said second electrode for generating a pulse having a duration in the range of 0.030 to 3 µs that causes generation of a submicrosecond duration discharge in a conducting medium between said wire and said second electrode with pulse energies in the range of 1–1000 µJ.

2. The device of claim 1, wherein said wire has an exit diameter of between 1 and 100 microns.

3. The device of claim 2, wherein said insulator is tapered.

4. The device of claim 3, wherein said insulator is pulled glass.

5. The device of claim 1, wherein said wire has an exit diameter of between 5 and 40 micrometers.

6. The device of claim 1, wherein said second electrode is a coating on said insulator.

7. The device of claim 1, wherein said second electrode has an outside diameter of less than 1 mm.

8. The device of claim 1, wherein said discharge has a duration sufficient to produce a cavitation bubble having a diameter of between 0.4 and 0.5 mm.

9. A device consisting of:
    a microelectrode formed of a single metal wire inside an insulator, said wire having an exit diameter of less than 100 microns;
    an electrode surrounding said metal wire and said insulator, said electrode having a diameter between 0.9 and 1.0 mm; and
    a high voltage pulse generator capable of producing a voltage in the range of 100 V to 10 kV connected to said wire for generating pulses having durations of between 30 ns and 3 µs to cause generation of submicrosecond duration sparks in a conductive medium between said wire and said electrode, the generated pulses having pulse energies in the range of 1–1000 µJ.

10. The device of claim 9 wherein said sparks produce cavitation bubbles having diameters of between 0.4 and 0.5 mm.

11. The device of claim 9, wherein said electrode comprises a conductive coating on said insulator.

12. The device of claim 9, further including a gap between said insulator and said electrode.

13. The device of claim 9, wherein said insulator is pulled glass to produce a tapered insulator and an exit wire diameter of between 1 and 100 microns, and wherein said electrode is a conductive coating on said insulator.

14. A device comprising:
    a microelectrode comprising a glass microcapillary having a metal wire inside the glass, the microcapillary being tapered to a point and coated with metal to form a concentric metal needle, said metal wire having an exit diameter in the range of 1–100 microns; and
    a high voltage pulse generator connected to said wire to generate a submicrosecond duration discharge in a conducting liquid containing medium with pulse energies in the range of 1–1000 µJ to produce a cavitation bubble, said discharge having a duration sufficiently short to produce a bubble having a diameter no greater than 0.5 mm in said conducting medium with characteristics that emulate the action of pulsed lasers in said conducting medium.

15. A device comprising:
    a microelectrode comprising a glass microcapillary having a metal wire inside the glass, the microcapillary being tapered to a point and coated with metal to form a concentric metal needle, said metal wire having an exit diameter of less than 100 microns; and
    a high voltage pulse generator connected to said wire to generate an electrical discharge having a duration in the range of 0.030 to 3.0 microsecond in a conducting liquid containing medium with pulse energies in the range of 1–1000 µJ to produce in said conducting medium submillimeter-sized cavitation bubbles with characteristics that emulate the action of pulsed lasers.

16. A device comprising:
    a microelectrode comprising a glass microcapillary having a metal wire inside the glass, the microcapillary being tapered to a point and coated with metal to form a concentric metal needle, said metal wire having an exit diameter in a range of 1–100 microns; and
    a high voltage pulse generator connected to said metal wire and having a pulse shaped to generate at the metal wire exit a submicrosecond duration electrical discharge through a gas layer in a conducting liquid containing environment with a pulse energy in the range of 1–1000 µJ to produce cavitation bubble generation in said conducting medium in a manner that produces cavitation bubbles which collapse after reaching a maximum diameter of 0.5 mm, with characteristics that emulate the action of pulsed lasers in said conducting medium.

17. A device as recited in claim 14, 15 or 16, further including a second electrode.

18. A device as recited in claim 14, 15 or 16, further including a second electrode, and a gap between said second electrode and said microelectrode for lifting treated tissue by suction of said medium through this gap, and the evacuation of gas bubbles and tissue debris that result from tissue cutting.

19. A device as in claim 14, 15 or 16, further including means for attachment to a catheter for the simultaneous delivery of drugs to a treated area.

20. A device as in claim 14, 15 or 16, in which said microelectrode is composed of multiple metal wires inside said insulator.

21. A device as in claim 14, 15 or 16, in which said microelectrode includes a tip which is bent at an angle with the axes of the microelectrode that can vary from a few degrees to as much as 180 degrees with respect to the microelectrode axis.

22. A device as in claim 14, 15 or 16, in which a tip of the microelectrode is bent in a manner that causes a resulting action at the surface of said medium to occur at an angle with the axis of said microelectrode, and wherein the axis of the microelectrode defines a cantilever that is flexible enough to bend and measure surface forces so that such a device can cause fine alterations on a surface with resolutions that can be sub-micrometer to nanometer in dimension.

23. A device as in claim 14, 15 or 16, in which the microelectrode has a flat tip or an angled tip.

24. A device as in claim 14, 15 or 16, in which the microelectrode has a round tip.

25. A device as in claim 14, 15 or 16, comprising an array of parallel microelectrodes generating a parallel array of cavitation bubbles.

* * * * *